United States Patent
Klatt et al.

(10) Patent No.: US 6,441,024 B1
(45) Date of Patent: Aug. 27, 2002

(54) CRYSTAL MODIFICATION OF LIPOIC ACID

(75) Inventors: Martin Jochen Klatt, Bad Dürkheim; Markus Niebel, Mannheim; Joachim Paust, Neuhofen; Jens Rieger, Ludwigshafen, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/743,920

(22) PCT Filed: Jul. 12, 1999

(86) PCT No.: PCT/EP99/04870

§ 371 (c)(1),
(2), (4) Date: Jan. 17, 2001

(87) PCT Pub. No.: WO00/08012

PCT Pub. Date: Feb. 17, 2000

(30) Foreign Application Priority Data

Jul. 31, 1998 (DE) .......................... 198 34 608

(51) Int. Cl.$^7$ ..................... A61K 31/385; C07D 339/04
(52) U.S. Cl. .......................... 514/440; 549/39
(58) Field of Search ............................ 514/440; 549/39

(56) References Cited

U.S. PATENT DOCUMENTS

| | | | |
|---|---|---|---|
| 5,281,722 A | 1/1994 | Blaschke et al. | 549/39 |
| 5,455,264 A | 10/1995 | Beisswenger et al. | 514/440 |
| 5,489,694 A | 2/1996 | Paust et al. | 549/39 |
| 5,530,143 A | 6/1996 | Balkenhohl et al. | 549/39 |
| 5,994,393 A | * 11/1999 | Beisswenger et al. | 514/440 |

FOREIGN PATENT DOCUMENTS

| | | |
|---|---|---|
| EP | 0 487 986 | 6/1992 |
| EP | 0 543 088 | 5/1993 |
| EP | 0 586 987 | 3/1994 |
| EP | 0 593 896 | 4/1994 |
| WO | WO 93/02187 | 2/1993 |

OTHER PUBLICATIONS

Reed et al. "Isolation, Characterization and Structure of α–Lipoic Acid" Journal of American Chemical Society vol. 75 (1953) pp. 1267–1270.

Page et al. "Enantioselective Synthesis of R–(+)–α–Lipoic Acid" J. Chem Soc., Chem Commun. (1986) pp. 1408–1409.

* cited by examiner

Primary Examiner—Deborah C. Lambkin
(74) Attorney, Agent, or Firm—Keil & Weinkauf

(57) ABSTRACT

In the 2 Θ diffractogram of an enantiomerically pure crystalline (R)- or (S)-lipoic acid, the most intense reflection line in the range from 13° to 30° is that at 2 Θ=23°.

8 Claims, 3 Drawing Sheets

CRYSTAL MODIFICATION OF LIPOIC ACID

This appliation is a 371 of PCT/EP99/04870 Jul. 12, 1999

The present invention relates to a process for preparing crystalline α-lipoic acid in high yields, a new crystal modification of α-lipoic acid and its use.

α-Lipoic acid is used in the food industry and in pharmaceutical formulations.

When lipoic acid is spoken of in the following, this always refers to the enantiomerically pure compounds ((R)- or (S)-lipoic acid).

Processes for preparing enantiomerically pure lipoic acid are described, for example, in Bulman-Page et al., J. Chem. Soc., Chem. Commun. 1986, 1409. Furthermore, the racemate can be prepared very effectively by the process described in EP 0 586 987. The resolution of the enantiomers can be carried out using chiral amines (e.g. EP 0 543 088). (R)-Lipoic acid can also be isolated from natural sources (Reed et al. JACS 1953 Vol. 75, 1267). (R)-Lipoic acid can also be prepared in enantiomerically pure form by the process described in EP 487 986.

The crude product is subsequently recrystallized from pentane, hexane or cyclohexane.

Alternatively, the crude product can be recrystallized from a 2:1 mixture of cyclohexane/ethyl acetate (EP 0 595 896).

Where the precise recrystallization conditions and yields are reported, a yield of 40%, based on the crude product, is obtained from cyclohexane at from 5 to 10° C., and a yield of 31%, based on the crude product, is obtained at about −15° C. from the cyclohexane/ethyl acetate mixture.

The previous processes for preparing pure crystalline (R)- or (S)-α-lipoic acid give yields which are unsatisfactory for industrial preparation of α-lipoic acid.

Increasing the yield by reuse of the mother liquor for the crystallization is technically complicated and generally leads to an increase in impurities which are highly undesirable in pharmaceutical processing or in the food industry.

It is an object of the present invention to develop a process for preparing pure, pharmaceutical-grade lipoic acid in a form favorable for pharmaceutical processing. The crystalline forms produced hitherto have the X-ray diffractograms [transmission X-ray diffractometer patterns recorded using Cu $K\alpha_1$" radiation (2 theta)] published by Reed et al. for (+)-alpha-lipoic acid from cyclohexane and in EP 0 593 896 (from cyclohexane/ethyl acetate).

We have found that this object is achieved by dissolving α-lipoic acid in an organic solvent having a dielectric constant $\epsilon$ from 1.95 to 2.4. The organic α-lipoic acid solution is then cooled to from 0 to −20° C., giving a crystalline form which is new for enantiomerically pure α-lipoic acid, has a new type of line intensity distribution in the X-ray diffractogram and is suitable for pharmaceutical processing. In addition, the product according to the present invention is obtained in a high purity (with <0.1% of impurities) and in yields of 75% or more. The invention can be applied both in the pharmaceutical industry and in the food industry where lipoic acid is used as a food additive and also in dietary supplements.

The most intense line in the range from 15 to 30° in the 2 Θ diffractogram of the crystalline product according to the present invention is a line at 23°. The crystalline products according to the present invention have an intensity ratio of 2 Θ=23° to 2 Θ=18.2° of at least 1.

In addition, the use of the solvents according to the present invention having a dielectric constant of from 1.95 to 2.4 has the additional advantage over those described in the literature that, in the crystallization, they give a very pure crystalline product in high yields. As solvents or components of solvent mixtures, it is possible to use, for example: straight-chain or branched, saturated or monounsaturated or polyunsaturated aliphatic hydrocarbons having a chain length of from $C_5$ to $C_8$, cycloaliphatic hydrocarbons such as cyclopentane, cyclohexane or methylcyclohexane, or monohalogenated or polyhalogenated, preferably chlorinated, hydrocarbons having a chain length of from 1 to 4 carbon atoms. It is possible to use either solvent mixtures such as technical-grade hexane or heptane in which hexane or heptane is the main component or else the pure solvents.

Preference is given to solvent mixtures of aliphatic and aromatic hydrocarbons.

Furthermore, substituted or unsubstituted, monocyclic and polycyclic aromatics are also possible as solvents or components of solvents. Examples which may be mentioned are toluene, o-, m-and p-xylene, ethylbenzene, propylbenzene and isopropylbenzene and mesitylene.

In addition, the solvents or solvent mixtures used according to the present invention have to have a melting point of less than 0° C., preferably less than −20° C., particularly preferably less than −40° C. Preference is also given to solvents which have a low toxicity, since the resulting lipoic acid is to be used as a drug or food additive.

The preferred upper limit for the dielectric constant is 2.2; particular preference is given to a range from 2.0 to 2.1.

The preferred upper limit for the temperature range of the crystallization is −50° C., particularly preferably −10°C.

The process can also be carried out at lower temperatures, as long as the solvent or solvent mixture does not become solid. A preferred lower temperature limit is −20° C.

Preferred solvent mixtures are those of toluene or xylene with $C_5$–$C_7$–aliphatics in a volume ratio of from 1:1 to 1:4; particular preference is given to a mixture of toluene and technical-grade hexane or toluene and technical-grade heptane.

The lipoic acid is recrystallized from a solvent or solvent mixture using a weight ratio of lipoic acid to solvent of preferably from 1:5 to 1:15, particularly preferably from 1:8 to 1:12.

In the case of a solvent mixture, the lipoic acid is preferably first dissolved in a polar mixture or in the polar solvent component and the remaining nonpolar solvent component for the recrystallization is then added before cooling to from 0 to −20 C.

In aqueous solution (1 g of lipoic acid in 20 ml of 1N NaOH), the product obtained according to the present invention has an absorbance of <0.300 (430 nm, path length =1 cm).

EXAMPLE 1

10 g of (R)-α-lipoic acid were introduced into 67 ml of a 1:1 solvent mixture of toluene/technical-grade hexane and at 50° C. This gave a solution which was filtered. The filtrate [sic] was washed with 33 ml of hexane (technical-grade). The combined solutions were held at from 0 to 5° C. for 1 hour in ice water and subsequently stirred for another 1 hour at about −15° C. while cooling with a mixture of ice/sodium chloride. The crystals were subsequently filtered off with suction and dried at room temperature under reduced pressure: 8.1 g of (R)-(+)-α-lipoic acid.

EXAMPLE 2

10 g of crude (R)-α-lipoic acid are dissolved in 35 ml of toluene at 50° C. 35 ml of technical-grade heptane are added, the solution is filtered at 50° C. through 4 g of silica gel F 60 and a further 35 ml of technical-grade heptane are added to the filtrate. The solution is cooled to from 0 to 5° C., seeded and, after 1 hour, cooled to −15° C. at a cooling rate of 5° C./h.

The desired product is isolated by suction filtration on a frit, the crystalline product is washed twice with 15 ml of technical-grade heptane and dried in a stream of nitrogen: 8.0 g of (R)-α-lipoic acid, m.p. 47.9–48.9° C.; $[\alpha]^{24}_D$= 113.7° C., c=1 in benzene, purity according to GC analysis= 99.95%; all trace components <0.05% by area.

The lipoic acids prepared according to the present invention were subjected to X-ray diffraction analysis using Cu K-alpha radiation.

Figure 1:
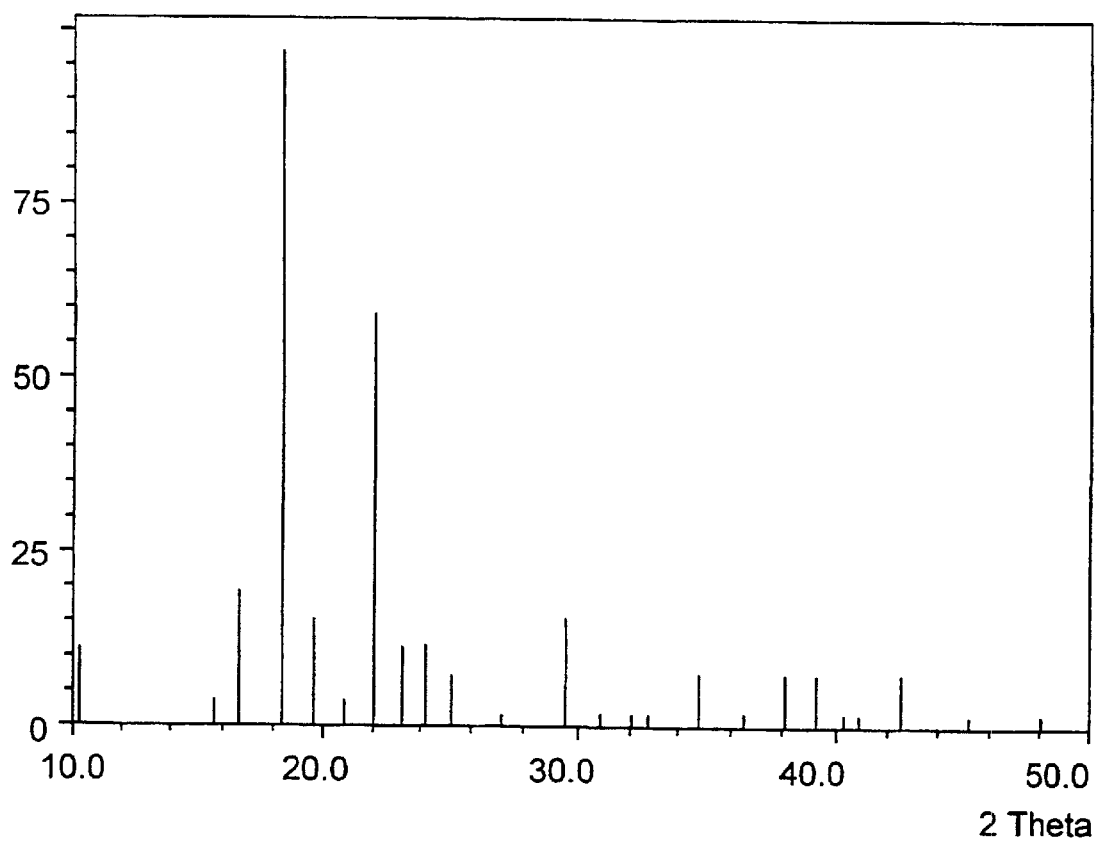
FIG. 1 shows a powder diffractogram of an (R)-lipoic acid of the prior art from cyclohexane.
Figure 2:
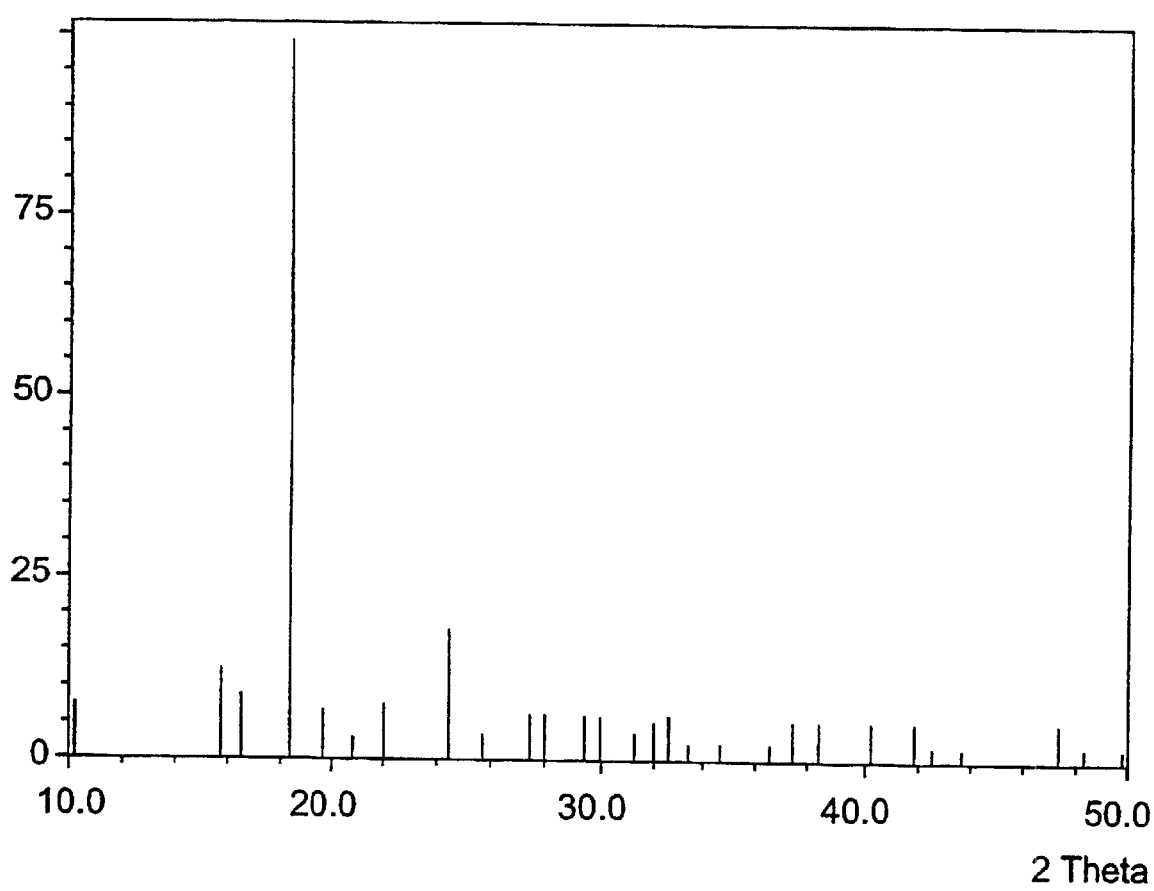
FIG. 2 shows a powder diffractogram of an (R)-lipoic acid of the prior art from cyclohexane/ethyl acetate.
Figure 3:
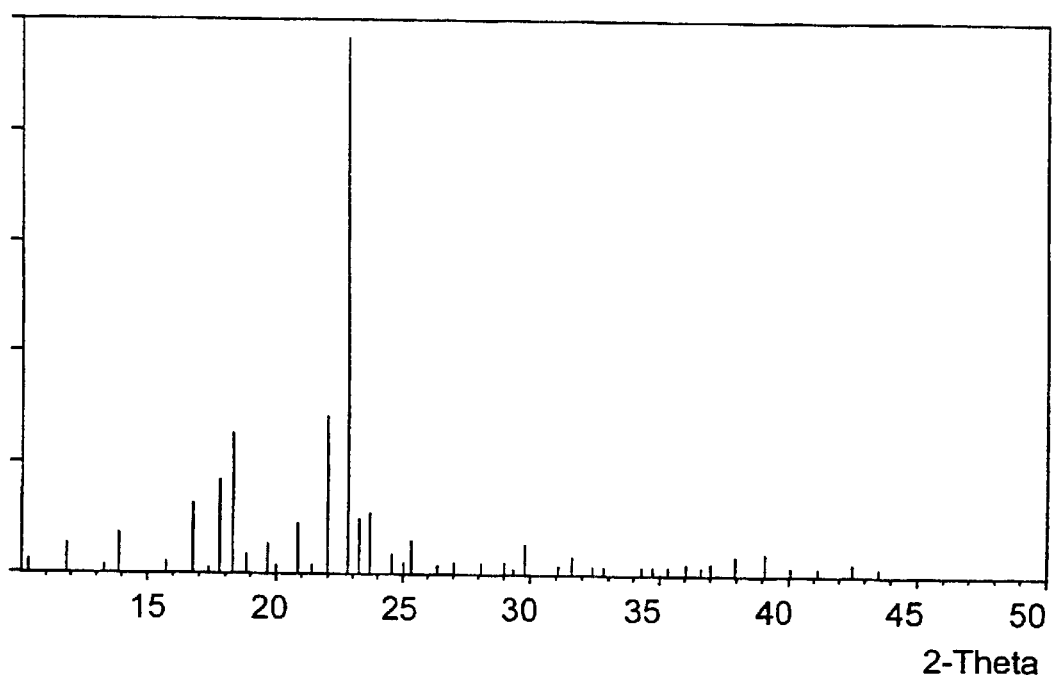
FIG. 3 shows a powder diffractogram of an (R)-lipoic acid of the present invention.

We claim:

1. Enantiomerically pure crystalline R- or S-lipoic acid for which the reflection line at 2 Θ=23° is the most intense in the range from 15° to 30° in the 2 Θdiffractogram.

2. A process for preparing crystalline lipoic acid, which comprises crystallizing the lipoic acid at from 0°C. to −20° C. from a solvent or solvent mixture which has a dielectric constant ε of from 1.95 to 2.4.

3. A process as claimed in claim 2, wherein a solvent mixture of aliphatic and aromatic hydrocarbons is used.

4. A process as claimed in claim 3, wherein the solvent mixture used is a mixture of toluene and hexane or a mixture of toluene and heptane.

5. R-Lipoic acid obtained by the process of claim 3.

6. Lipoic acid obtained by the process of claim 2.

7. A drug composition containing an effective amount of lipoic acid prepared by the process of claim 1.

8. A food additive or a dietary supplement containing an effective amount of lipoic acid prepared by the process of claim 1.

* * * * *